(12) United States Patent
Chatterjee et al.

(10) Patent No.: US 12,412,671 B2
(45) Date of Patent: Sep. 9, 2025

(54) METHOD AND SYSTEM FOR CLASSIFICATION OF COGNITIVE LOAD USING DATA OBTAINED FROM WEARABLE SENSORS

(71) Applicant: Tata Consultancy Services Limited, Mumbai (IN)

(72) Inventors: Debatri Chatterjee, Kolkata (IN); Dibyanshu Jaiswal, Kolkata (IN); Ramesh Kumar Ramakrishnan, Bangalore (IN); Rahul Dasharath Gavas, Bangalore (IN); Arpan Pal, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 643 days.

(21) Appl. No.: 17/808,468

(22) Filed: Jun. 23, 2022

(65) Prior Publication Data

US 2022/0415521 A1 Dec. 29, 2022

(30) Foreign Application Priority Data

Jun. 23, 2021 (IN) .............................. 202121028199

(51) Int. Cl.
*G06N 20/00* (2019.01)
*G16H 40/67* (2018.01)
*G16H 50/70* (2018.01)

(52) U.S. Cl.
CPC ............. *G16H 50/70* (2018.01); *G06N 20/00* (2019.01); *G16H 40/67* (2018.01)

(58) Field of Classification Search
None
See application file for complete search history.

(56) References Cited

U.S. PATENT DOCUMENTS

2019/0138806 A1* 5/2019 Banerjee ........... G06F 16/24568
2019/0175091 A1* 6/2019 Das ...................... A61B 5/0533
(Continued)

OTHER PUBLICATIONS

Jaiswal etl al. "Effective Assessment of Cognitive Load in Real-World Scenarios using Wrist-worn Sensor Data" BodySys'21: Proceedings of the Workshop on Body-Centric Computing Systems pp. 7-12 https://doi.org/10.1145/3469260.3469666 (Year: 2021).*

(Continued)

*Primary Examiner* — Jonathan Ng
(74) *Attorney, Agent, or Firm* — FINNEGAN, HENDERSON, FARABOW, GARRETT & DUNNER LLP (57) ABSTRACT

This disclosure relates generally to a method and system for classification of cognitive load (CL) using data obtained from wearable sensors. The disclosed method uses a multimodal based approach using wrist-worn sensors for real time monitoring of CL in real world scenarios and improves the accuracy of detection of CL. A set of distinguishing features are selected from physiological signals received from the wrist-worn sensors. These features are used for training a classification model for classifying the CL of a patient into a no load or a high load. The set of distinguishing features are selected from domain specific features and signal property based generic features of the physiological signals. The disclosed method is used for classification of CL in scenarios such as to check how the cognitive load of a candidate varies during interviews, to assess the participants workload during online meetings and so on.

15 Claims, 5 Drawing Sheets

(56) References Cited

U.S. PATENT DOCUMENTS

| | | | | |
|---|---|---|---|---|
| 2020/0383624 | A1* | 12/2020 | Jaiswal | G16H 50/30 |
| 2021/0022656 | A1* | 1/2021 | Khasnobish | A61B 5/7267 |
| 2021/0319899 | A1* | 10/2021 | Liu | A61B 5/055 |
| 2021/0393182 | A1* | 12/2021 | Chatterjee | G06N 20/00 |

OTHER PUBLICATIONS

Gavas et al., "Multivariate Variational Mode Decomposition based approach for Blink Removal from EEG Signal," 2020 IEEE International Conference on Pervasive Computing and Communications Workshops (PerCom Workshops), Austin, TX, USA, 2020, (Year: 2020).*

Giannakakkis etl al. "A stress recognition system using HRV parameters and machine learning techniques" 2019 8th International Conference on Affective Computing and Intelligent Interaction Workshops and Demos (ACIIW), Cambridge, UK, 2019, pp. 269-272, doi: 10.1109/ACIIW.2019.8925142. (Year: 2019).*

Banerjee et al. "Reckoning respiratory signals to affectively decipher mental state" Annu Int Conf IEEE Eng Med Biol Soc. Jul. 2019; 2019:4654-4659. doi: 10.1109/EMBC.2019.8857498. PMID: 31946901. (Year: 2019).*

Gjoreski et al. "Cognitive Load Monitoring With Wearables-Lessons Learned From a Machine Learning Challenge" in IEEE Access, vol. 9, pp. 103325-103336, 2021 (Year: 2021).*

Borisov, Vadim et al., "Robust cognitive load detection from wrist-band sensors", Computers in Human Behavior Reports, Date: Jun. 2021, vol. 4, Publisher: Science Direct, https://www.scienedirect.com/sdfe/reader/pii/S2451958821000646/pdf.

Gjoreski, Martin et al., "Datasets for Cognitive Load Inference Using Wearable Sensors and Psychological Traits", Applied Sciences, Date: May 2020, vol. 10(11), Publisher: MDPI, https://www.mdpi.com/2076-3417/10/11/3843.

Alani, Ali A. et al., "Classifying Imbalanced Multi-modal Sensor Data for Human Activity Recognition in a Smart Home using Deep Learning", International Joint Conference on Neural Networks (IJCNN), Date: Jul. 2020, Publisher: IEEE, https://core.ac.uk/download/pdf/326503014.pdf.

Gjoreski, Martin et al., "Cognitive Load Monitoring with Wearables—Lessons Learned from a Machine Learning Challenge", IEEE Access, Date: 2020, Publisher: IEEE, https://ieeexplore.ieee.org/stamp/stamp.jsp?arnumber=9466833.

* cited by examiner

METHOD AND SYSTEM FOR CLASSIFICATION OF COGNITIVE LOAD USING DATA OBTAINED FROM WEARABLE SENSORS

PRIORITY CLAIM

This U.S. patent application claims priority under 35 U.S.C. § 119 to: Indian Patent Application No. 202121028199, filed on Jun. 23, 2021. The entire contents of the aforementioned application are incorporated herein by reference.

TECHNICAL FIELD

The disclosure herein generally relates to the field of cognitive load analysis, and, more particularly, to a method and system for classification of cognitive load using data obtained from wearable sensors.

BACKGROUND

Cognitive load (CL) or mental workload is the amount of mental resources required to execute a task. It is a multi-dimensional construct, consisting of factors like nature of task, characteristics of the participant, task demands, and actual cognitive capacity or resources allocated to the task. Limited working memory capacity of human result in either under-load or overload conditions based on the amount of information processed while executing the task. High CL might degrade task performance, thereby developing conditions like stress/anxiety. Whereas low CL is under-utilization of cognitive resources, may also cause boredom while doing the task. In scenarios like job interview or call center interactions, if the CL of one person can be assessed by the other person, then certain changes can be made by the other person to make the interaction more pleasant and effective. Another example could be an online tutorial system, where personalized contents can be provided based on the CL of the user to provide better learning experience. It is well known that people perform best when they are at their psychological best. Thus, assessment of cognitive load in real time is an important research problem.

Traditionally, CL is assessed using methods such as i) self-report questionnaires like NASA Task Load Index (NASA-TLX) or ii) task performance-based measures. Self-report questionnaires are highly subjective and requires experts for administration and interpretation of results. Task performance is a secondary measure based approach and provides a rough estimate only. More importantly, these approaches are not suitable for real-time assessment of CL in the real world scenarios. Various other approaches have also been used for measurement of CL. Subjective ratings are most widely used approach where the amount of CL experienced by people are rated on a Likert scale. Another approach is based on performance based measures such as a task completion time and a rate of correct answers. These approaches are convenient to implement, but the accuracy is hugely impacted by subject specific bias. Moreover, these methods can be used only after completion of the task and hence, are not useful for continuous assessment of the cognitive load.

With recent advancements in sensor technology, physiological sensors are being used for assessment of CL. Most widely used sensors sense physiological signals such as brain signals, galvanic skin conductance, heart rate, respiration rate and so on. However, most of these sensors are expensive and hence are not suitable for mass deployment. Some low cost wearable sensors are available which can read the above mentioned physiological signals but may result in lower quality. In an approach for assessment of CL condition, skin conductance levels measured using such low cost wearable sensors were used to differentiate between a stress condition and a high CL condition in an office environment. Though various physiological responses have been used for studying CL, none of the approaches using single physiological signal was found to be sufficient to characterize the CL in an accurate manner.

SUMMARY

Embodiments of the present disclosure present technological improvements as solutions to one or more of the above-mentioned technical problems recognized by the inventors in conventional systems. For example, in one embodiment, a method for classification of cognitive load using data obtained from wearable sensors is provided. The method includes: providing a plurality of physiological signals collected from a plurality of subjects through a plurality of wearable sensors as training data for training a classification model for classification of cognitive load, wherein each of the plurality of physiological signals are prelabelled as one of (i) a first class or (ii) a second class; extracting (i) a plurality of domain specific features and (ii) a plurality of signal property based generic features as a plurality of features from the plurality of physiological signals using a multi-level approach; selecting a set of optimal features from the plurality of features using a maximal information coefficient algorithm and a minimum redundancy maximum relevance algorithm; augmenting the training data by artificially inducing class imbalance between the first class and the second class; applying a synthetic minority over-sampling technique on the augmented training data to generate a set of synthetic data; training the classification model using (i) the training data and (ii) the set of synthetic data to classify the cognitive load as one of (i) a low load or (ii) a high load; obtaining via a wearable device a set of physiological signals from a subject for classifying in real time the cognitive load of the subject; obtaining the set of optimal features from the set of physiological signals of the subject; and classifying the cognitive load using the trained classification model as one of (i) the low load or (ii) the high load.

In another aspect, a system for classification of cognitive load using data obtained from wearable sensors is provided. The system comprises memory storing instructions; one or more communication interfaces; and one or more hardware processors coupled to the memory via the one or more communication interfaces, wherein the one or more hardware processors are configured by the instructions to provide a plurality of physiological signals collected from a plurality of subjects through a plurality of wearable sensors as training data for training a classification model for classification of cognitive load, wherein each of the plurality of physiological signals are prelabelled as one of (i) a first class or (ii) a second class; extract (i) a plurality of domain specific features and (ii) a plurality of signal property based generic features as a plurality of features from the plurality of physiological signals using a multi-level approach; select a set of optimal features from the plurality of features using a maximal information coefficient algorithm and a minimum redundancy maximum relevance algorithm; augment the training data by artificially inducing class imbalance between the first class and the second class; apply a synthetic minority over-sampling technique on the augmented training data to generate a set of synthetic data; train the classification model using (i) the training data and (ii) the set of synthetic data to classify the cognitive load as one of (i) a low load or (ii) a high load; obtain via a wearable device a set of physiological signals from a subject for classifying in real time the cognitive load of the subject; obtain the set of optimal features from the set of physiological signals of the subject; and classify the cognitive load using the trained classification model as one of (i) the low load or (ii) the high load.

In an embodiment, wherein the plurality of physiological signals comprises (i) Galvanic skin response, (ii) Heart rate, (iii) RR interval and (iv) skin temperature.

In an embodiment, wherein generating the synthetic data comprises, obtaining a first set of physiological signals amongst the plurality of physiological signals prelabelled as the first class; obtaining a half of a second set of physiological signals amongst the plurality of physiological signals prelabelled as the second class; and applying the synthetic minority over-sampling technique over the first set of physiological signals and the second set of physiological signals to generate the synthetic data.

In an embodiment, wherein the set of optimal features are one or more of (i) a set of discrete wavelet transform (DWT) features and (ii) a set of short term Fourier transform features.

In an embodiment, wherein the set of discrete wavelet transform (DWT) features comprises variance, kurtosis and skewness, mean, difference of mean, box-pierce statistics, hurst exponent, difference of skewness, kurtosis of windowed DWT, zero crossing, and standard deviation of windowed DWT.

In an embodiment, wherein the set of short term Fourier transform features comprises kurtosis of fast Fourier transform (FFT) coefficient, difference of skewness of windowed FFT, difference of kurtosis of windowed FFT, mean, spectral centroid, linear prediction, total harmonic distortion, hurst exponent, and linear prediction.

In yet another aspect, there is provided a computer program product comprising a non-transitory computer readable medium having a computer readable program embodied therein, wherein the computer readable program, when executed on a computing device causes the computing device for classification of cognitive load using data obtained from wearable sensors by providing a plurality of physiological signals collected from a plurality of subjects through a plurality of wearable sensors as training data for training a classification model for classification of cognitive load, wherein each of the plurality of physiological signals are prelabelled as one of (i) a first class or (ii) a second class; extracting (i) a plurality of domain specific features and (ii) a plurality of signal property based generic features as a plurality of features from the plurality of physiological signals using a multi-level approach; selecting a set of optimal features from the plurality of features using a maximal information coefficient algorithm and a minimum redundancy maximum relevance algorithm; augmenting the training data by artificially inducing class imbalance between the first class and the second class; applying a synthetic minority over-sampling technique on the augmented training data to generate a set of synthetic data; training the classification model using (i) the training data and (ii) the set of synthetic data to classify the cognitive load as one of (i) a low load or (ii) a high load; obtaining via a wearable device a set of physiological signals from a subject for classifying in real time the cognitive load of the subject; obtaining the set of optimal features from the set of physiological signals of the subject; and classifying the cognitive load using the trained classification model as one of (i) the low load or (ii) the high load.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Currently many methods exist for studying the effect of Cognitive Load (CL) for diverse applications. Multimedia/online learning addresses questions like how an individual processes information, how they learn through multimedia approaches and how to choose appropriate instructional design for an individual for avoiding the cognitive overload, resulting in better learning outcome. Some prior works performed an analysis of CL for group meetings. Public speaking or giving presentations is a necessary part of jobs like sales, management, teaching and the like and is often regarded as a stressful activity.

There are many prior works which does an analysis on the impact of CL on individuals. One of the prior works analyzed the impact of awareness of audience's cognitive state during a presentation. The work concluded that this awareness has a positive effect on anxiety and confidence level of the presenter and reduces their mental workload. In another prior work the CL of a candidate was assessed during a technical interview. The insight about candidate's mental workload, helps the interviewer to design a better interview process and to have better visibility of cognitive abilities of the candidate. Increased mental workload over a prolonged period of time affects the overall mental health of an individual and degrades the job performance by increasing failures or error rates. All the prior works show that there is a close interconnection between CL and affective inferences like emotion and stress. Increased cognitive demand decreases the neural activation in response to emotional stimuli as both emotion and cognition processes share same neural networks of human brain. Hence it is important to assess the cognitive load of individuals in real world scenario.

The embodiments herein provide a method and system for classification of cognitive load in real world scenarios using data obtained from wearable sensors. The disclosed method is used for classification of CL in scenarios such as to understand the interactions between customers and service provider in call centers, to check how the cognitive load of a candidate varies during interviews or to assess the participants workload during online meetings, workshops or tutorials and so on. Such scenarios of classification of CL shall not be construed as limiting the scope of the present disclosure. The method uses a multi-modal based approach using wrist-worn sensors for real time monitoring of CL in real world scenarios. The disclosed method improves the accuracy of detection of CL.

Referring now to the drawings, and more particularly to FIG. 1 through FIG. 4, where similar reference characters denote corresponding features consistently throughout the figures, there are shown preferred embodiments and these embodiments are described in the context of the following exemplary system and/or method.

Figure 1:
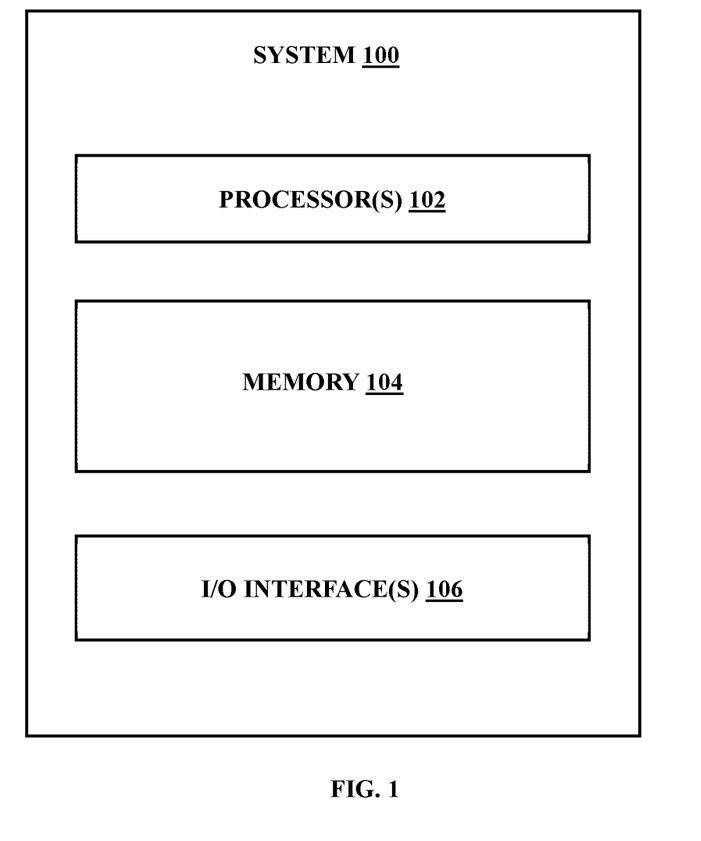
FIG. 1 illustrates an exemplary block diagram of a system for classification of cognitive load using data obtained from wearable sensors, in accordance with some embodiments of the present disclosure

FIG. 1 illustrates a system 100 for classification of cognitive load using data obtained from wearable sensors. In an embodiment, the system 100 includes one or more processors 102, communication interface device(s) or input/output (I/O) interface(s) 106, and one or more data storage devices or memory 104 operatively coupled to the one or more processors 102. The memory 104 comprises one or more modules 108. The one or more processors 102 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In the context of the present disclosure, the expressions 'processors' and 'hardware processors' may be used interchangeably. In an embodiment, the system 100 can be implemented in a variety of computing systems, such as laptop computers, notebooks, hand-held devices, workstations, mainframe computers, servers, a network cloud and the like.

The I/O interface (s) 106 may include a variety of software and hardware interfaces, for example, a web interface, a graphical user interface, and the like and can facilitate multiple communications within a wide variety of networks and protocol types, including wired networks, for example, LAN, cable, etc., and wireless networks, such as WLAN, cellular, or satellite. In an embodiment, the I/O interface(s) can include one or more ports for connecting a number of devices to one another or to another server.

The memory 104 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 104 includes a module for classification of cognitive load using wearable sensor data of the system 100 along with a plurality of modules (not shown) to perform the methodology described herein.

Figure 2:
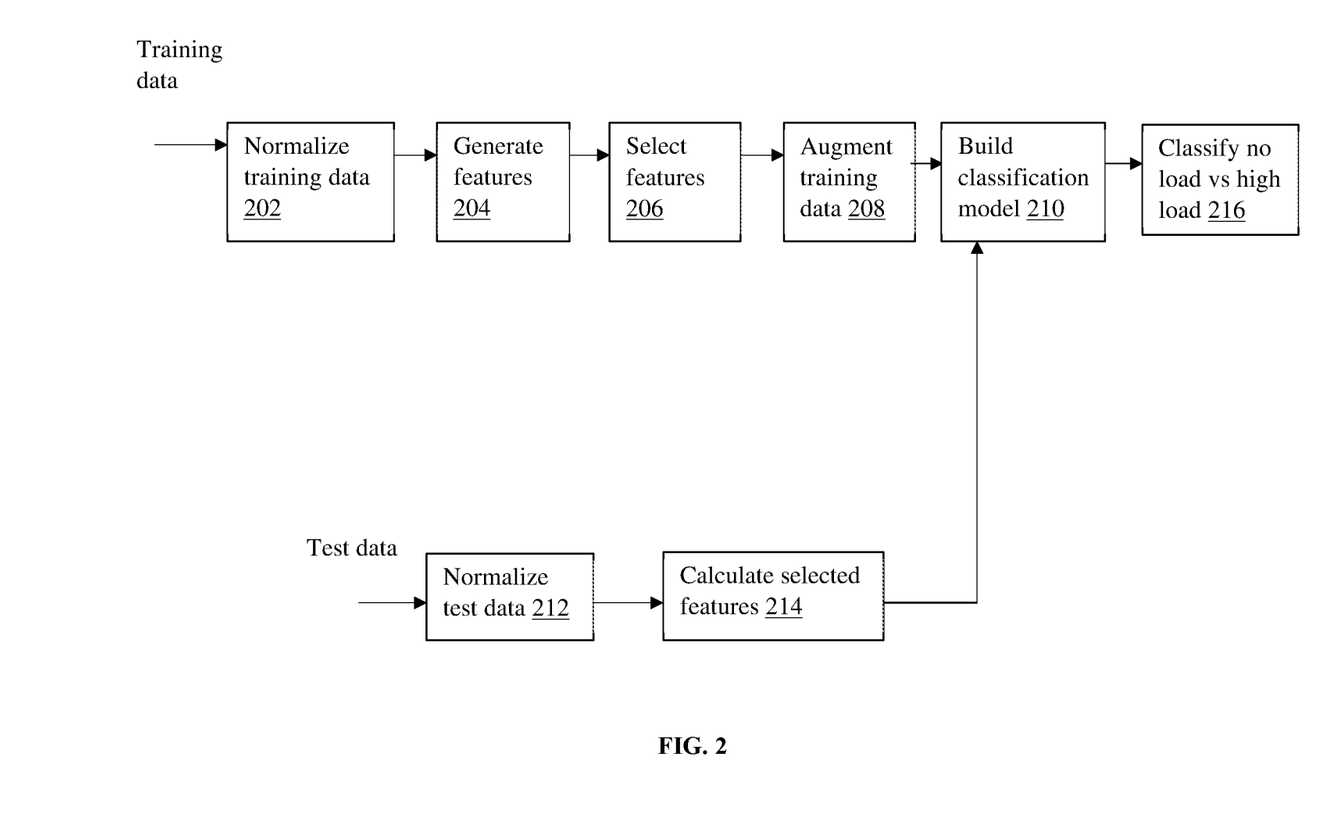
FIG. 2 is an exemplary flow diagram for classification of cognitive load using data obtained from wearable sensors according to some embodiments of the present disclosure.

FIG. 2 is an exemplary flow diagram for classification of cognitive load using data obtained from wearable sensors according to some embodiments of the present disclosure. The flow diagram depicts a training phase for building a classification model for classifying the CL using training data and a testing phase for classifying the CL using the built classification model using test data. The training phase in the disclosed method receives training data comprising physiological signals from wearable sensors of a subject. At step 202, the training data from each sensor is further normalized using subject specific minimum and maximum values. At step 204 these normalized training data is used to generate a set of features from which at step 206 the most distinguishing features used for classification are selected. At step 208 the selected features were augmented to increase the training data size and are used for building a classification model at step 210 by using the training data and the augmented training data. In the testing phase of the flow diagram, test data for classifying CL of a subject using the built classification model is received. At step 212 the test data is normalized and further at step 214 the set of already selected most discriminating features are calculated from the normalized test data to classify at step 216 the CL as "no load" or "high load" using the classification model built during the training phase.

Figure 3A:
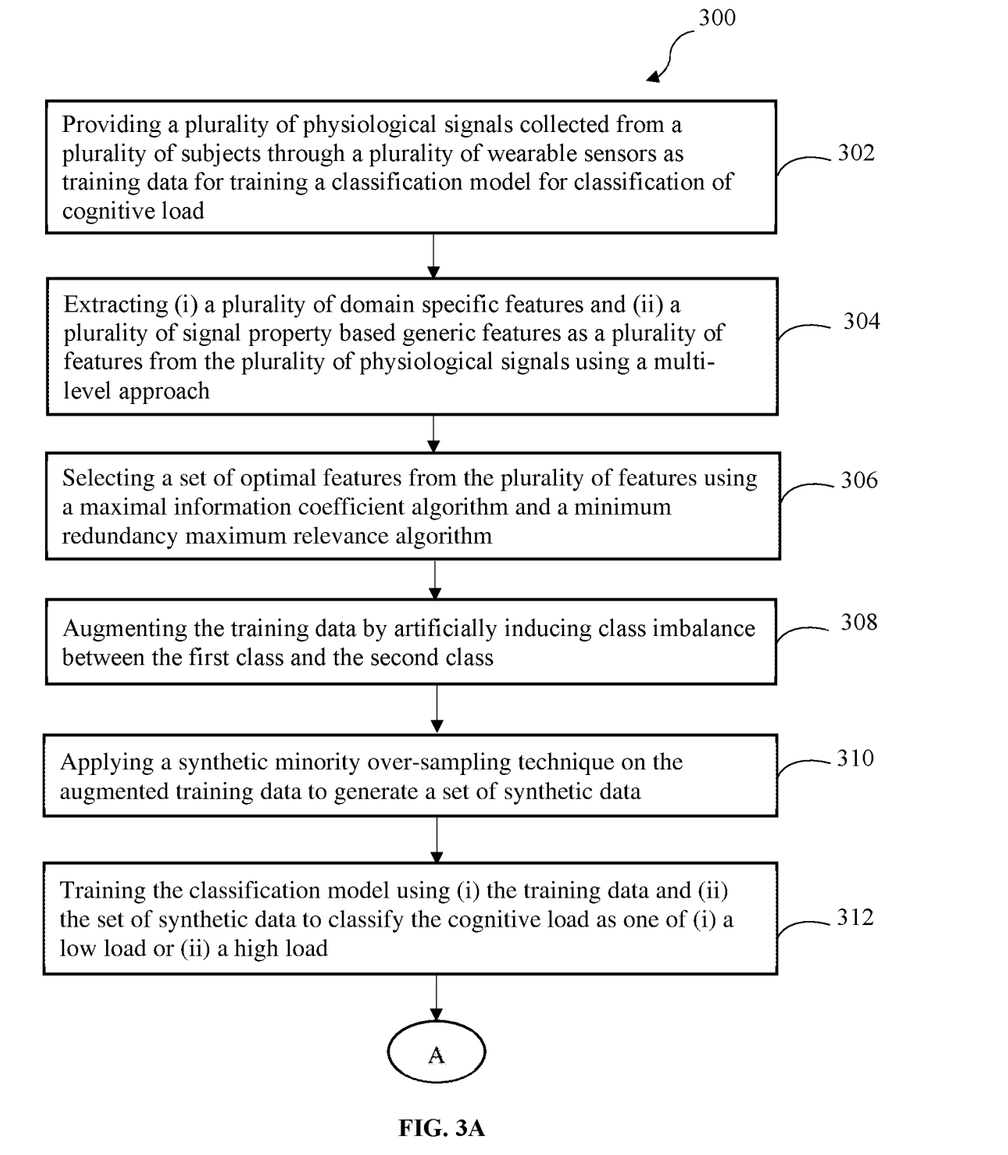
FIG. 3A and FIG. 3B is an exemplary flow diagram illustrating steps of method for training a classification model for classifying cognitive load using data obtained from wearable sensors according to some embodiments of the present disclosure.
Figure 3B:
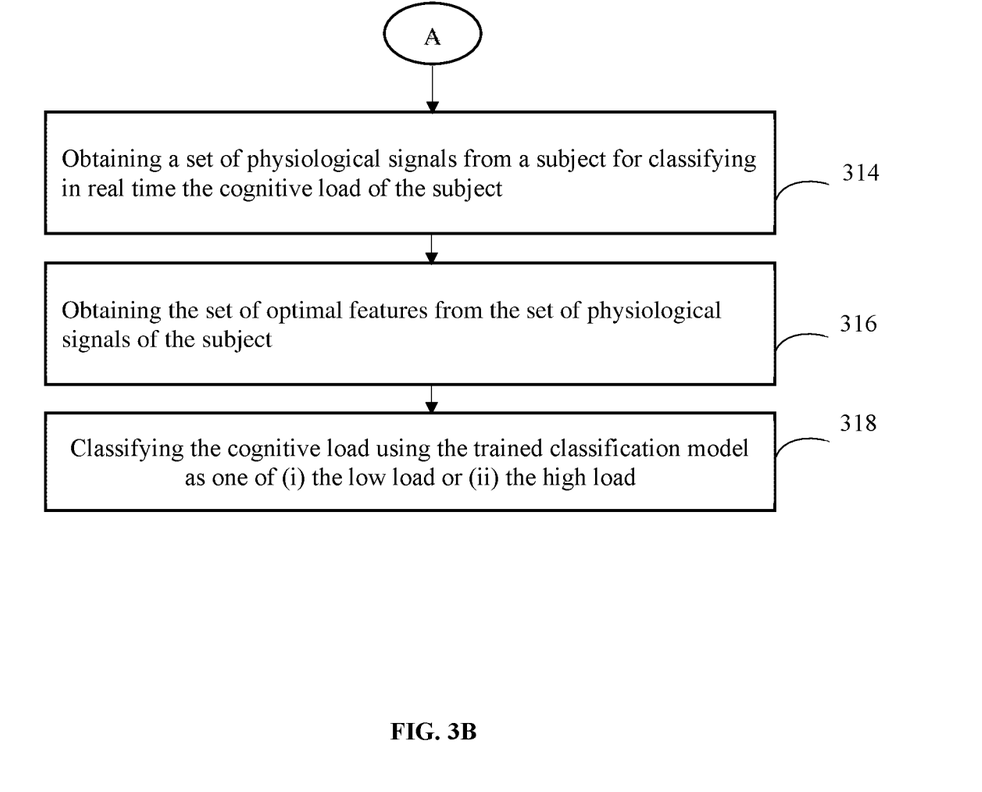

FIG. 3A and FIG. 3B is an exemplary flow diagram illustrating steps of the method 300 for training a classification model for classifying cognitive load using data obtained from wearable sensors according to some embodiments of the present disclosure.

In an embodiment of the present disclosure, the one or more processors 102 are configured to provide at step 302, a plurality of physiological signals collected from a plurality of subjects through a plurality of wearable sensors as training data for training a classification model for classification of cognitive load. Each of the plurality of physiological signals are prelabelled as one of (i) a first class or (ii) a second class. The plurality of physiological signals considered include heart rate (HR), RR intervals (RR), galvanic skin response (GSR) and skin temperature (TEMP). The dataset used for training phase of the disclosed method is CogLoad dataset which comprises of physiological signals recorded from 23 subjects using Microsoft band 2. The CogLoad dataset includes HR, RR, GSR and TEMP signals.

The disclosed method considers rest interval as "no load" condition (first class) whereas the task interval is considered as "high load" condition (second class). The sensor signals (GSR, HR, RR and TEMP) of the dataset were initially re-sampled to a uniform frequency of 1 Hz. Further the data from each sensor were normalized using subject specific minimum and maximum values.

In an embodiment of the present disclosure, the one or more processors 102 are configured to extract at step 304, (i) a plurality of domain specific features and (ii) a plurality of signal property based generic features as a plurality of features from the plurality of physiological signals using a multi-level approach. Normalized sensor data were subdivided into a number of windows of duration 30 seconds. A set of time and frequency domain features along with some signal property based generic features are extracted on each window. The plurality of features extracted from each sensor are listed in Table 1.

TABLE 1

| Sensor | Domain | Features |
| --- | --- | --- |
| GSR | Time Domain | Min, max, standard deviation, kurtosis, skewness, no. of peaks, sum of positive derivatives, signal moments |
| | Frequency domain | mean & median, frequency, power at mean & median, frequency, tonic & phasic power |
| | Response | square average. of tonic & phasic component, relative power, mean tonic & phasic power, accumulated GSR, power in 0.04-0.4 Hz. |
| HR | Time domain | Mean, max, min, standard deviation, skewness, kurtosis, variance |
| RR | Time domain | Mean, SDRR, RMSSD, pNN20, pNN50, poin-care parameters |
| TEMP | Time domain | Mean, Min, max, skewness |

The features are extracted in a multi-level approach. At Level 1, time domain features, Short term Fourier transform (STFT) based features and Discrete wavelet transform (DWT) based features are extracted. In level 2, spectral, statistical, peak-trough features are extracted from level 1 features. Spectral features include centroid, crest factor, decrease, flatness, flux, kurtosis, roll-off, skewness, slope and spread. Statistical features used are mean, variance, standard deviation, root mean square, skewness, kurtosis. Finally, in level 3, ratios and derivatives of the level 2 features are computed. In total, 392 generic features are generated for a sensor time series data. Since there are four types of sensor data, hence, in total 392×4=1568 generic features are generated.

In an embodiment of the present disclosure, the one or more processors 102 are configured to select at step 306, a set of optimal features from the plurality of features using a maximal information coefficient algorithm and a minimum redundancy maximum relevance algorithm. The set of optimal features are selected for maximizing the classification accuracy. For feature selection, standard Maximal information coefficient (MIC) and Minimum Redundancy Maximum Relevance (mRMR) algorithms are used. Features listed in Table 1 along with 1568 generic features are used to recommend a set of 50 features. Features selected for each sensor are listed in Table 2.

TABLE 2

| Sensor | Feature Type | Features |
| --- | --- | --- |
| GSR | DWT (9) | Variance, kurtosis & skewness, Difference of mean, box-pierce stats, hurst exponent. |
| | STFT (2) | Kurtosis of FFT coefficient, Difference of skewness of windowed FFT |
| HR | DWT (9) | Skewness, kurtosis, hurst exponent, Difference, of skewness and kurtosis of windowed DWT, box-pierce statistics |
| | STFT (1) | Difference of kurtosis of windowed FFT, |
| RR | DWT (16) | Mean, skewness, variance, Zero crossing, rms, box-pierce statistics, Hurst exponent, Difference of mean, skewness, standard deviation of windowed DWT, |
| | STFT (7) | Mean, spectral centroid, linear prediction, total harmonic distortion |
| TEMP | DWT (4) | Mean, mean & skewness of windowed DWT |
| | STFT (2) | Hurst exponent, linear prediction. |

In an embodiment of the present disclosure, the one or more processors 102 are configured to augment at step 308, the training data by artificially inducing class imbalance between the first class and the second class. Synthetic minority over-sampling technique (SMOTE) is used to increase data size and variety of the training data. SMOTE is an oversampling approach used to handle class imbalance (i.e., the observations in one of the classes is much higher/lower compared to that of the other class). It randomly increases minority class examples, by introducing new instances between existing minority instances based on k-nearest neighbor approach. Cogload dataset is a balanced dataset. Hence, imbalance is artificially induced into the dataset by taking all the instances of a particular class (say first class) with half of the instances of the other class (i.e., second class) and performed SMOTE. This approach doubles the size of the original instances. The characteristics of the augmented data was analyzed using Kullback-Leibler (KL) divergence, log-cluster and cross-classification.

In an embodiment of the present disclosure, the one or more processors 102 are configured to apply at step 310, the SMOTE on the augmented training data to generate a set of synthetic data. Synthetic data is generated by obtaining, a first set of physiological signals amongst the plurality of physiological signals prelabelled as the first class. Further a half of a second set of physiological signals amongst the plurality of physiological signals prelabelled as the second class is obtained and then synthetic data is generated by applying the synthetic minority over-sampling technique over the first set of physiological signals and the second set of physiological signals.

In an embodiment of the present disclosure, the one or more processors 102 are configured to train at step 312, the classification model using (i) the training data and (ii) the set of synthetic data to classify the cognitive load as one of (i) a low load or (ii) a high load. The classification model is trained and built using the training data and the set of synthetic data. Several classifiers such as TreeBagger (RF), Support vector Machine (SVM), K Nearest Neighbor (KNN), random forest classifier, AdaBoost and so on may be used for classification.

In an embodiment of the present disclosure, the one or more processors 102 are configured to obtain at step 314, using a wearable sensor, a set of physiological signals from a subject for classifying in real time the cognitive load of the subject. The physiological signals comprising GSR, HR, RR and TEMP are obtained from the wearable sensor of the subject.

In an embodiment of the present disclosure, the one or more processors 102 are configured to obtain at step 316, the set of optimal features from the set of physiological signals of the subject. The features selected (as shown in Table 2) from the physiological signals are used for performing classification.

In an embodiment of the present disclosure, the one or more processors 102 are configured to classify at step 318, the cognitive load using the trained classification model as one of (i) the low load or (ii) the high load.

To check the performance of the classification model for completely unseen data, 80-20 split is performed for training data and testing data. Out of 23 participants, 5 participants (i.e., 20%) are chosen randomly as test participants. The classification model was built from sensor data of remaining 18 (i.e., 80%) participants. Sensor data of 5 test participants were first normalized using subject specific minimum and maximum values. Further the rest and task data were subdivided into a number of windows of duration 30 seconds.

All 50 recommended features were extracted for each of these windows. Finally, these features were fed to the trained classification model to get the final predictions (i.e., no-load/high-load) for each test instance.

Experimental Results

Sensor specific domain features along with 1568 SPGF features are generated of which 50 features were selected as the most significant features. The features selected for each sensor is shown in Table 2. It is observed that most distinguishing sensor is RR data (23 features) and less distinguishing sensor is TEMP (6 features). DWT based features are most distinguishing ones for all the sensors. For DWT, Daubechies (db4) mother wavelet is used for breaking down the signal into two parts. Component of low pass filter is called approximate coefficient and component of high pass filter is called details coefficient. Most of the DWT features selected were high frequency detail coefficients. These 50 features are used for further processing and building the classification model for classifying cognitive load.

To check the characteristics of augmented data, Kullback-Leibler (KL) divergence, log cluster and cross classification are calculated. KL divergence over a pair of probability mass functions (PMF) gives a measure of the similarity between two PMFs. If KL is zero, the distributions are regarded as identical. Larger value of KL signifies larger discrepancy between two PMFs. For calculating log cluster, instances having similar values are placed in a particular group. The instances created from real data and synthetic data are merged together and a metric is calculated. Larger value of the metric indicates larger discrepancy between real and synthetic data. Lastly, cross-classification approach is used to measure the differences between statistical structures of real and synthetic data. In first step, training was done using 70% of the real data and testing was done using 30% of real and synthetic data. Classification performance thus indicates the similarities between statistical properties of real and synthetic data. Next, training was done using 70% of the synthetic data and testing was done using same 30% of real and synthetic data. The classification performance indicates if the inferences drawn from the synthetic data can be applied to real data. Finally, we calculated percentage relative classification difference (pRCD) as $$pRCD = 100 \times \frac{|A_s - A_r|}{A_s} \quad (1)$$

where $A_s$ is the classification accuracy using synthetic data for training, $A_r$ is the classification accuracy using real data for training. Lower value of pRCD indicates distribution of real and synthetic data is identical. Values of these metrics for domain and recommended features are shown in Table 3. Small values of these metrics indicate that the characteristics of data generated using the disclosed approach, is similar to the real data.

TABLE 3

| Dataset | Features used | Log cluster | pRCD | KL div |
|---|---|---|---|---|
| CogLoad | Domain features | −4.09 | 2.56 | 18.7 |
| | Recommended 50 features | −5.48 | 4.46 | 9.69 |

Figure 4:
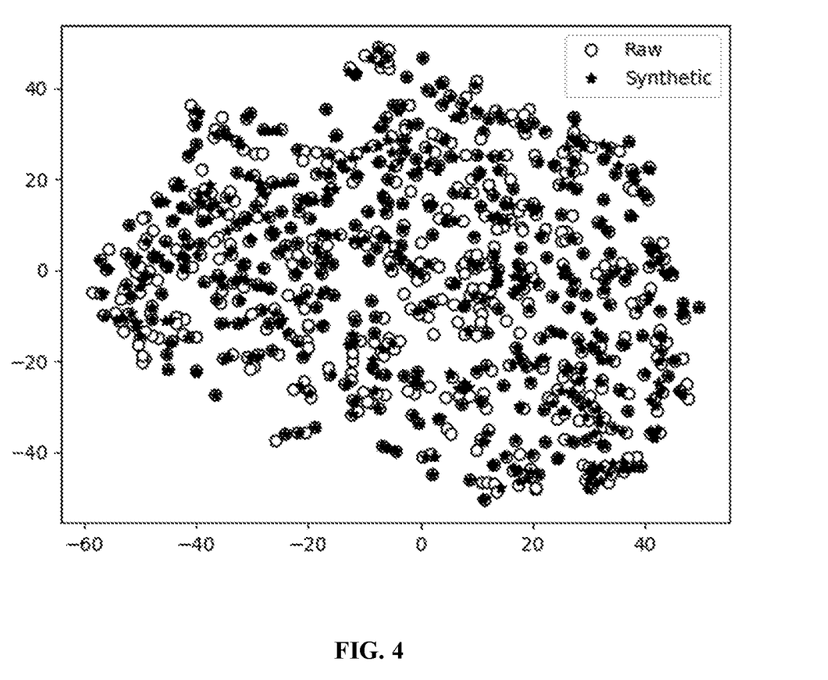
FIG. 4 illustrates a t-distributed stochastic neighbor embedding (tSNE) plot for real and augmented data showing uniform distribution in accordance with some embodiments of the present disclosure.

FIG. 4 illustrates a t-Distributed Stochastic Neighbor Embedding (tSNE) plot for real and augmented data showing uniform distribution in accordance with some embodiments of the present disclosure. The t-SNE method which is a non-linear technique is used for dimensional reduction and helps in the visualization of high-dimensional data. FIG. 4 shows that the two data sets belong to same cluster indicating that the synthetic data set aligns very well with the raw data. Thus, it can be concluded that the distribution data generated by the disclosed augmentation approach are identical with real data, thereby achieving the goals of larger volume and higher variety within the boundaries of the real data.

The classification model of the disclosed method is compared with state-of-the-art approaches and the classification performance on test data is analyzed. The augmented sensor data of 23 participants are used for building the cognitive load classification model. The comparison of the disclosed approach with state-of-the-art approaches is presented in Table 4. The classification accuracy of the first two state-of-the-art methods which have used the same dataset, are approximately 63% and 68%, respectively. However, with recommended feature set, the disclosed method achieved a classification accuracy of 86% using 6 fold cross validation (6FCV) approach and 69.5% using leave one session out (LOSO) approach respectively. Thus, by using same number of features, the disclosed method performed better than the first two state-of-the-art methods.

TABLE 4

| Approach | No. of Features | validation approach | Accuracy (%) |
|---|---|---|---|
| State-of-the-art Method 1 | 50 | LOSO | 68 |
| State-of-the-art Method 2 | 49 | 6 FCV | 63.2 |
| Disclosed recommended features | 50 | 6 FCV | 86 |
| method with | | LOSO | 69.5 |

Finally, the classification model is used to classify unseen data of test participants. Average classification accuracy obtained for 5 test participants are reported in the Table 5. The accuracy using features used in various literature is only 64.7% whereas the accuracy using our recommended features on raw data is 66.5%. Maximum classification accuracy of 69% is achieved using recommended features on augmented data which is our disclosed method. Moreover, the sensitivity and specificity obtained are also very much balanced. Since the classification model performs well on unseen data, it can work well in real world scenarios.

TABLE 5

| Features | No. of features | Feature type | Accuracy (%) | Sensitivity | Specificity |
|---|---|---|---|---|---|
| Domain features | 83 | Raw | 64.7 | 0.71 | 0.57 |
| Recommended | 50 | Raw | 66.5 | 0.73 | 0.61 |
| Recommended | 50 | With data augment | 69 | 0.75 | 0.63 |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method comprising the steps of:

providing, via one or more hardware processors, a plurality of physiological signals collected from a plurality of subjects through a plurality of wearable sensors as training data for training a classification model for classification of cognitive load, wherein each of the plurality of physiological signals are prelabelled as one of (i) a first class or (ii) a second class, wherein the training data is a balanced dataset, and wherein the plurality of physiological signals comprises (i) Galvanic skin response, (ii) Heart rate, (iii) RR interval and (iv) skin temperature;

extracting, via the one or more hardware processors, (i) a plurality of domain specific features and (ii) a plurality of signal property based generic features as a plurality of features from the plurality of physiological signals using a multi-level approach, wherein the multi-level approach comprises:

extracting time domain features, short term Fourier transform (STFF) based features, and Discrete wavelet transform (DWT) based features in a first level, extracting spectral, statistical, peak-trough features in a second level based on feature extracted in the first level, and computing ratios and derivatives in a third level, from the features extracted in the second level;

selecting, via the one or more hardware processors, a set of optimal features from the plurality of features using a maximal information coefficient algorithm and a minimum redundancy maximum relevance algorithm;

augmenting, via the one or more hardware processors, the training data by artificially inducing class imbalance between the first class and the second class, wherein the class imbalance is induced by taking all instances of the first class with half of instances of the second class;

applying, via the one or more hardware processors, a synthetic minority over-sampling technique on the augmented training data to generate a set of synthetic data;

training, via the one or more hardware processors, the classification model using (i) the training data and (ii) the set of synthetic data to classify the cognitive load as one of (i) a low load or (ii) a high load;

obtaining, via a wearable device, a set of physiological signals from a subject for classifying in real time the cognitive load of the subject;

obtaining, via the one or more hardware processors, the set of optimal features from the set of physiological signals of the subject;

classifying, via the one or more hardware processors, the cognitive load using the trained classification model as one of (i) the low load or (ii) the high load; and monitoring, in real time via the one or more hardware processors, the cognitive load of the subject based on the classification of the cognitive load using the trained classification model to analyze the cognitive load of the subject in real world scenarios including analyzing the cognitive load of the subject during one of an interview, an online meeting, a workshop, and a tutorial.

2. The method of claim 1, wherein generating the synthetic data comprises, obtaining, via the one or more hardware processors, a first set of physiological signals amongst the plurality of physiological signals prelabelled as the first class;

obtaining, via the one or more hardware processors, a half of a second set of physiological signals amongst the plurality of physiological signals prelabelled as the second class; and applying, via the one or more hardware processors, the synthetic minority over-sampling technique over the first set of physiological signals and the second set of physiological signals to generate the synthetic data.

3. The method of claim 1, wherein the set of optimal features are one or more of (i) a set of discrete wavelet transform (DWT) features and (ii) a set of short term Fourier transform features.

4. The method of claim 1, wherein the set of discrete wavelet transform (DWT) features comprises variance, kurtosis and skewness, mean, difference of mean, box-pierce statistics, hurst exponent, difference of skewness, kurtosis of windowed DWT, zero crossing, and standard deviation of windowed DWT.

5. The method of claim 1, wherein the set of short term Fourier transform features comprises kurtosis of fast Fourier transform (FFT) coefficient, difference of skewness of windowed FFT, difference of kurtosis of windowed FFT, mean, spectral centroid, linear prediction, total harmonic distortion, hurst exponent, and linear prediction.

6. A system, comprising:
a memory storing instructions;
one or more communication interfaces; and
one or more hardware processors coupled to the memory via the one or more communication interfaces, wherein the one or more hardware processors are configured by the instructions to:
provide a plurality of physiological signals collected from a plurality of subjects through a plurality of wearable sensors as training data for training a classification model for classification of cognitive load, wherein each of the plurality of physiological signals are prelabelled as one of (i) a first class or (ii) a second class, wherein the training data is a balanced dataset, and wherein the plurality of physiological signals comprises (i) Galvanic skin response, (ii) Heart rate, (iii) RR interval and (iv) skin temperature;
extract (i) a plurality of domain specific features and (ii) a plurality of signal property based generic features as a plurality of features from the plurality of physiological signals using a multi-level approach, wherein to use the multi-level approach, the one or more hardware processors are configured by the instructions to:
extract time domain features, short term Fourier transform (STFF) based features, and Discrete wavelet transform (DWT) based features in a first level,
extract spectral, statistical, peak-trough features in a second level based on feature extracted in the first level, and
compute ratios and derivatives in a third level, from the features extracted in the second level;
select a set of optimal features from the plurality of features using a maximal information coefficient algorithm and a minimum redundancy maximum relevance algorithm;
augment the training data by artificially inducing class imbalance between the first class and the second class, wherein the class imbalance is induced by taking all instances of the first class with half of instances of the second class;
apply a synthetic minority over-sampling technique on the augmented training data to generate a set of synthetic data;
train the classification model using (i) the training data and (ii) the set of synthetic data to classify the cognitive load as one of (i) a low load or (ii) a high load;
obtain a set of physiological signals from a subject for classifying in real time the cognitive load of the subject;
obtain the set of optimal features from the set of physiological signals of the subject;
classify the cognitive load using the trained classification model as one of (i) the low load or (ii) the high load; and
monitor, in real time, the cognitive load of the subject based on the classification of the cognitive load using the trained classification model to analyze the cognitive load of the subject in real world scenarios including analyzing the cognitive load of the subject during one of an interview, an online meeting, a workshop, and a tutorial.

7. The system of claim 6, wherein generating the synthetic data comprises, obtaining, via the one or more hardware processors, a first set of physiological signals amongst the plurality of physiological signals prelabelled as the first class;

obtaining, via the one or more hardware processors, a half of a second set of physiological signals amongst the plurality of physiological signals prelabelled as the second class; and applying, via the one or more hardware processors, the synthetic minority over-sampling technique over the first set of physiological signals and the second set of physiological signals to generate the synthetic data.

8. The system of claim 6, wherein the set of optimal features are one or more of (i) a set of discrete wavelet transform (DWT) features and (ii) a set of short term Fourier transform features.

9. The system of claim 6, wherein the set of discrete wavelet transform (DWT) features comprises variance, kurtosis and skewness, mean, difference of mean, box-pierce statistics, hurst exponent, difference of skewness, kurtosis of windowed DWT, zero crossing, and standard deviation of windowed DWT.

10. The system of claim 6, wherein the set of short term Fourier transform features comprises kurtosis of fast Fourier transform (FFT) coefficient, difference of skewness of windowed FFT, difference of kurtosis of windowed FFT, mean, spectral centroid, linear prediction, total harmonic distortion, hurst exponent, and linear prediction.

11. One or more non-transitory machine-readable information storage mediums comprising one or more instructions which when executed by one or more hardware processors cause:

provinding, a plurality of physiological signals collected from a plurality of subjects through a plurality of wearable sensors as training data for training a classification model for classification of cognitive load, wherein each of the plurality of physiological signals are prelabelled as one of (i) a first class or (ii) a second class, wherein the training data is a balanced dataset, and wherein the plurality of physiological signals comprises (i) Galvanic skin response, (ii) Heart rate, (iii) RR interval and (iv) skin temperature;

extracting, via the one or more hardware processors, (i) a plurality of domain specific features and (ii) a plurality of signal property based generic features as a plurality of features from the plurality of physiological signals using a multi-level approach, wherein the multi-level approach comprises:

extracting time domain features, short term Fourier transform (STFF) based features, and Discrete wavelet transform (DWT) based features in a first level, extracting spectral, statistical, peak-trough features in a second level based on feature extracted in the first level, and computing ratios and derivatives in a third level, from the features extracted in the second level;

selecting, via the one or more hardware processors, a set of optimal features from the plurality of features using a maximal information coefficient algorithm and a minimum redundancy maximum relevance algorithm;

augmenting, via the one or more hardware processors, the training data by artificially inducing class imbalance between the first class and the second class, wherein the class imbalance is induced by taking all instances of the first class with half of instances of the second class;

applying, via the one or more hardware processors, a synthetic minority over-sampling technique on the augmented training data to generate a set of synthetic data;

training, via the one or more hardware processors, the classification model using (i) the training data and (ii) the set of synthetic data to classify the cognitive load as one of (i) a low load or (ii) a high load;

obtaining, via a wearable device, a set of physiological signals from a subject for classifying in real time the cognitive load of the subject;

obtaining, via the one or more hardware processors, the set of optimal features from the set of physiological signals of the subject;

classifying, via the one or more hardware processors, the cognitive load using the trained classification model as one of (i) the low load or (ii) the high load; and monitoring, in real time via the one or more hardware processors, the cognitive load of the subject based on the classification of the cognitive load using the trained classification model to analyze the cognitive load of the subject in real world scenarios including analyzing the cognitive load of the subject during one of an interview, an online meeting, a workshop, and a tutorial.

12. The one or more non-transitory machine-readable information storage mediums of claim 11, wherein generating the synthetic data comprises, obtaining, via the one or more hardware processors, a first set of physiological signals amongst the plurality of physiological signals prelabelled as the first class;

obtaining, via the one or more hardware processors, a half of a second set of physiological signals amongst the plurality of physiological signals prelabelled as the second class; and applying, via the one or more hardware processors, the synthetic minority over-sampling technique over the first set of physiological signals and the second set of physiological signals to generate the synthetic data.

13. The one or more non-transitory machine-readable information storage mediums of claim 11, wherein the set of optimal features are one or more of (i) a set of discrete wavelet transform (DWT) features and (ii) a set of short term Fourier transform features.

14. The one or more non-transitory machine-readable information storage mediums of claim 11, wherein the set of discrete wavelet transform (DWT) features comprises variance, kurtosis and skewness, mean, difference of mean, box-pierce statistics, hurst exponent, difference of skewness, kurtosis of windowed DWT, zero crossing, and standard deviation of windowed DWT.

15. The one or more non-transitory machine-readable information storage mediums of claim 11, wherein the set of short term Fourier transform features comprises kurtosis of fast Fourier transform (FFT) coefficient, difference of skewness of windowed FFT, difference of kurtosis of windowed FFT, mean, spectral centroid, linear prediction, total harmonic distortion, hurst exponent, and linear prediction.

* * * * *